US009475739B2

(12) United States Patent
Tirtowidjojo et al.

(10) Patent No.: US 9,475,739 B2
(45) Date of Patent: *Oct. 25, 2016

(54) PROCESS FOR THE PRODUCTION OF CHLORINATED PROPENES

(75) Inventors: Max M. Tirtowidjojo, Lake Jackson, TX (US); Barry B. Fish, Lake Jackson, TX (US); David S. Laitar, Midland, MI (US)

(73) Assignee: BLUE CUBE IP LLC, Midland, MI (US)

( * ) Notice: Subject to any disclaimer, the term of this patent is extended or adjusted under 35 U.S.C. 154(b) by 184 days.

This patent is subject to a terminal disclaimer.

(21) Appl. No.: 14/236,286

(22) PCT Filed: Aug. 1, 2012

(86) PCT No.: PCT/US2012/049203
§ 371 (c)(1),
(2), (4) Date: Jan. 30, 2014

(87) PCT Pub. No.: WO2013/022676
PCT Pub. Date: Feb. 14, 2013

(65) Prior Publication Data
US 2014/0163266 A1 Jun. 12, 2014

Related U.S. Application Data

(60) Provisional application No. 61/515,957, filed on Aug. 7, 2011.

(51) Int. Cl.
C07C 17/25 (2006.01)
C07C 17/10 (2006.01)
C07C 17/20 (2006.01)
C07C 17/06 (2006.01)
C07C 17/23 (2006.01)
C07C 17/093 (2006.01)

(52) U.S. Cl.
CPC .............. C07C 17/20 (2013.01); C07C 17/06 (2013.01); C07C 17/10 (2013.01); C07C 17/23 (2013.01); C07C 17/25 (2013.01); C07C 17/093 (2013.01)

(58) Field of Classification Search
CPC ...... C07C 17/25; C07C 17/093; C07C 17/10
USPC .................................................. 570/229, 253
See application file for complete search history.

(56) References Cited

U.S. PATENT DOCUMENTS

| 2,119,484 A | 5/1938 | Levine |
| 2,179,378 A | 11/1939 | Metzger |
| 2,207,193 A | 7/1940 | Groll |
| 2,299,441 A | 10/1942 | Vaughan |
| 2,302,228 A | 11/1942 | Kharasch |
| 2,370,342 A | 2/1945 | Zellner |
| 2,378,859 A | 6/1945 | Martin |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A | 9/1956 | Monroe |
| 2,765,359 A | 10/1956 | Pichler |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |

(Continued)

FOREIGN PATENT DOCUMENTS

| CH | 609022 | 6/1974 |
| CN | 101215220 | 7/2008 |

(Continued)

OTHER PUBLICATIONS

Fields et al., "Thermal Isomerization of 1,1-dichlorocyclopropanes", Chemical Communications (London) No. 21, Jan. 1, 1967, p. 1081.
Nguyen et al., Condensation de chloroforme avec des olefins fluorees en milieu basique, Journal of Fluorine Chemistry, vol. 55, No. 3, Dec. 1, 1991, pp. 241-248.
Shelton et al., "Addition of Halogens and Halogen Compounds to Allylic Chlorides. I. Addition of Hydrogen Halides", Journal of Organic Chemistry, Sep. 1958, pp. 1876-1880, vol. 23.

(Continued)

Primary Examiner — Elvis O Price
(74) Attorney, Agent, or Firm — Polsinelli PC

(57) ABSTRACT

Processes for the production of chlorinated propenes are provided. The present processes make use of a feedstock comprising 1,2,3-trichloropropane and chlorinates the 1,1,2,3-tetrachloropropane generated by the process prior to a dehydrochlorination step. Production of the less desirable pentachloropropane isomer, 1,1,2,3,3-pentachloropropane, is thus minimized. The present processes provide better reaction yield as compared to conventional processes that require dehydrochlorination of 1,1,2,3-tetrachloropropane prior to chlorinating the same. The present process can also generate anhydrous HCl as a byproduct that can be removed from the process and used as a feedstock for other processes, while limiting the production of waste water, thus providing further time and cost savings.

14 Claims, 2 Drawing Sheets

(56) References Cited

U.S. PATENT DOCUMENTS

| | | |
|---|---|---|
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |
| 3,954,410 A | 5/1976 | Pohl |
| 4,038,372 A | 7/1977 | Colli |
| 4,046,656 A | 9/1977 | Davis et al. |
| 4,051,182 A | 9/1977 | Pitt |
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Muller |
| 4,716,255 A | 12/1987 | Muller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Muller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada |
| 7,345,209 B2 | 3/2008 | Mukhopadhyay |
| 7,371,904 B2 | 5/2008 | Ma |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel |
| 8,058,490 B2 | 11/2011 | Strebelle |
| 8,071,825 B2 | 12/2011 | Johnson |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Kruper |
| 8,258,355 B2 | 9/2012 | Merkel |
| 8,357,828 B2 | 1/2013 | Okamoto |
| 8,367,867 B2 | 2/2013 | Zardi |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,558,041 B2 | 10/2013 | Tirtowidjojo et al. |
| 8,581,011 B2 | 11/2013 | Tirtowidjojo |
| 8,581,012 B2 | 11/2013 | Tirtowidjojo et al. |
| 8,614,361 B2 | 12/2013 | Suzuki |
| 8,614,363 B2 | 12/2013 | Wilson et al. |
| 8,907,148 B2 | 12/2014 | Tirtowidjojo et al. |
| 8,926,918 B2 | 1/2015 | Tirtowidjojo et al. |
| 8,933,280 B2 | 1/2015 | Tirtowidjojo et al. |
| 8,957,258 B2 | 2/2015 | Okamoto et al. |
| 9,056,808 B2 | 6/2015 | Tirtowidjojo et al. |
| 9,067,855 B2 | 6/2015 | Grandbois et al. |
| 2001/0018962 A1 | 9/2001 | Joshi |
| 2002/0110711 A1 | 8/2002 | Boneberg |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0265368 A1 | 11/2007 | Rao |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0088547 A1 | 4/2009 | Schamshurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0172472 A1 | 7/2011 | Sakyu |
| 2011/0218369 A1 | 9/2011 | Elsheikh |
| 2011/0251425 A1 | 10/2011 | Penzel |
| 2012/0065434 A1 | 3/2012 | Nose |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowidjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |

(56) References Cited

FOREIGN PATENT DOCUMENTS

| | | |
|---|---|---|
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 A1 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 A | 10/2006 |
| JP | 2007-021396 | 2/2007 |
| JP | 2008-063314 | 3/2008 |
| JP | 2009-000592 A | 1/2009 |
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 02059536 A1 | 8/2002 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 6/2012 |
| WO | 2012166393 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Tobey et al., "Pentachlorocyclopropane 1" Journal of the American Chemical Society, vol. 88, No. 11, Jun. 1, 1996 pp. 2478-2481.
Stevens, "Some New Cyclopropanes with a Note on the Exterior Valence Angles of Cyclopropane", JACS, Vo. 68, No. 4, 1945, 620-622.
Ochi, et al., "Preparation of Chloropropenes by Photochemical Dehydrochlorination of 1,2-Dichloropropane", Chemical Abstracts, Jul. 17, 1989, p. 574, 111(3).
Levanova, et al., "Cholorination of Chloroolefins C3-C4", Doklady Chemistry, vol. 386, No. 4, 2002, 496-498.
Bai et al., "Isomerization of Tetrachloropropene to Promote Utilization Ratio of Triallate Raw Materials", Petrochemical Technology & Application, 2007, 25(1).
Boualy et al., "Kharasch Addition of Tetrachloromethane to Alkenes Catalyzed by Metal Acetylacetonates", Catalysis Communications, 2011, pp. 1295-1297, vol. 12.
Chai et al., "Study of Preparation of 1,1,1,3-tetrachloropropane", Zhejiang Chemical Industry, 2010, pp. 1-3, 41(5).
Cristiano et al., "Tetraalkylphosphonium Trihalides. Room Temperature Ionic Liquids as Halogenation Reagents", J. Org. Chem., 2009, pp. 9027-9033, vol. 74.
Evstigneev et al., "Initiated Chlorination of Tetrachloropropane", Khim. Prom., 1984, pp. 393-394, 16(7).
Galitzenstein et al., "The Dehydrochlorination of Propylene Dichloride", Journal of the Society of Chemical Industry, 1950, pp. 298-304, vol. 69.
Gault et al., "Chlorination of Chloroform", Comptes Rendus Des Seances De L'Academie des Sciences, 1924, pp. 467-469, vol. 179.
Gerding et al., "Raman Spectra of aliphatic chlorine compounds II. Chloroethenes and Chloropropenes", RECUEIL,Jan. 1, 1955, pp. 957-975, vol. 74.
Hatch et al., "Allylic Chlorides. XV. Preparation and Properties of the 1,2,3-Trichloropropenes", JACS, Jan. 5, 1952, pp. 123-126, 74(1).
Hatch et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).
Herzfelder, "Substitution in the Aliphatic Series", Berichte der Deutschen Chemischen Gesellschaft, May-Aug. 1893, pp. 1257-1261, 26(2).
Ivanov et al., "Metal Phthalocyanine-Catalyzed Addition of Polychlorine-Containing Organic Compounds to C=C Bonds", Russian Chemical Bulletin, International Edition, Nov. 2009, pp. 2393-2396, 58(11).
Kang et al., "Kinetics of Synthesis of 1,1,1,3,3-pentachlorobutane Catalyzed by Fe—FeCl3", Chemical Research and Application, Jun. 2011, pp. 657-660, 23(6).
Kharasch et al., "Chlorinations with Sulfuryl Chloride. I. The Peroxide-Catalyzed Chlorination of Hydrocarbons", JACS, 1939, pp. 2142-2150, vol. 61.
Khusnutdinov et al., "CCl4 Attachment to Olefins Catalyzed by Chromium and Ruthenium Complexes. Impact of Water as a Nucleophilic Admixture", Oil Chemistry, 2009, pp. 349-356, vol. 4.
Kruper et al., "Synthesis of alpha-Halocinnamate Esters via Solvolytic Rearrangement of Trichloroallyl Alcohols", J. Org. Chem., 1991, pp. 3323-3329, vol. 56.
Leitch, "Organic Deuterium Compounds: V. The chlorination of propyne and propyne D-4", Canadian Journal of Chemistry, Apr. 1, 1953, pp. 385-386, 30(4).
Levanova et al., "Thermocatalytic Reactions of Bromochloropropanes", Russian Journal of Physical Chemistry, Jan. 1, 1983, pp. 1142-1146, vol. 57.
Liu et al., "Progress in the Synthesis of 1,1,1,3-tetrachloropropane", Guangzhou Chemicals, 2011, pp. 41-42, 39(5).
McBee et al., "Utilization of Polychloropropanes and Hexachloroethane", Industrial and Engineering Chemistry, Feb. 1, 1941, pp. 176-181, 33(2).
Mouneyrat, "Effect of Chlorine on Propyl Chloride in the Presence of Anhydrous Aluminum Chloride" Bulletin de la Societe Chimique de Paris, Jan. 1, 1899, pp. 616-623, 3(21).
Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.
Nair et al., "Atom Transfer Radical Addition (ATRA) of Carbon Tetrachloride and Chlorinated Esters to Various Olefins Catalyzed by CP'Ru(PPh3)(PR3)Cl Complexes", Inorganica Chimica Acta, 2012, pp. 96-103, vol. 380.
Nikishin et al., "Reactions of Methanol and Ethanol", Seriya Khimicheskaya, Dec. 1966, pp. 2188-2192, vol. 12.
Pozdnev et al., "Chlorination of Chloroform and the Conversion of Methylene Chloride Manufacture Still Residues", Khim., Khim. Tekhnol., 1970, 70(4).
Rotshtein et al., "Isomer Distribution on Chlorination of Chloropropanes", Zhurnal Organicheskoi Khimii, Sep. 1966, pp. 1539-1542, 2(9).
Semenov et al., "Selectivity of Photochemical Chlorination of Chloromethane in the Liquid Phase", Zhurnal Prikladnoi Khimii, Apr. 1985, pp. 840-845, 58(4).

(56) References Cited

OTHER PUBLICATIONS

Skell et al., "Reactions of BrCl with Alkyl Radicals", Tetrahedron Letters, 1986, pp. 5181-5184, 27(43).

Skell et al., "Selectivities of pi and sigma-Succinimidyl Radicals in Aubstitution and Addition Reactions. Appendix: Response to Walling, El-Taliawi and Zhao", JACS, Jul. 1, 1983, pp. 5125-5131, 105(15).

Tanuma et al., "Partially Fluorinated Metal Oxide Catalysts for a Friedel-Crafts-type Reaction of Dichlorofluoromethane with Tetrafluoroethylene", Catalysis Letters, 2010, pp. 77-82, vol. 136.

Urry et al., "Free-Radical Reactions of Diazomethane with Reactive Bromopolychloroalkanes", JACS, May 5, 1964, pp. 1815-1819, 86(9).

Wang, "Elimination Reactions of Polyhalopropanes under Emulsion Catalytic Conditions to give Halopropenes", Synthesis, Jun. 1982, pp. 494-496, vol. 6.

Zhao et al, "Research Progress on Preparation Technology of 1,1,2,3-Tetrachloropropene", Zhejiang Chemical Industry, 2010, pp. 8-10, 41(8).

Zheng et al., "Review of the Preparation of the low GWP alternative 1,3,3,3-tetrafluoropropene", Zhejiang Chemical Industry, 2010, pp. 5-7, 41(3).

Michigan Technological Univ., "Free-Radical Chlorination with Sulfuryl Chloride", Nov. 15, 2001, 1-7.

PROCESS FOR THE PRODUCTION OF CHLORINATED PROPENES

FIELD

The present invention relates to processes for the production of chlorinated propenes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoro-olefin (HFO) products. Relative to their predecessors, HFOs are expected to exert less impact on the atmosphere in the form of a lesser, or no, detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, chlorinated propenes, which may also find use as feedstocks for the manufacture of polyurethane blowing agents, biocides and polymers.

Unfortunately, many chlorinated propenes may have limited commercial availability, and/or may only be available at prohibitively high cost, due at least in part to the complicated, multi-step processes typically utilized in their manufacture. For example, in methods that utilize allyl chloride or 1,2,3-trichloropropane as starting materials, successive dehydrochlorinations and chlorinations with elemental chlorine may be done until the desired number of chlorine atoms has been added. Or, some conventional methods call for the chlorination of chlorinated alkanes having fewer chlorine atoms than desired in the final product.

At some point in many, if not all, such processes, mixtures of isomers of tetrachloropropanes and pentachloropropanes may typically be produced, that once produced, may either be difficult to remove and/or react to produce undesirable by products. And so, many conventional processes call for the removal of these isomers, thereby lowering the yield of such processes. And, doing so introduces additional cost and time to an already multi-step and typically expensive process. Additionally, such processes may also result in the production of large amounts of contaminated waste water having high quantities of sodium chloride, and one or more chlorinated organic(s). The waste water thus must typically be treated before releasing it to the environment, requiring even further expenditure. Any recovered sodium chloride provides little in the way of recoverable cost.

It would thus be desirable to provide improved processes for the production of chlorocarbon precursors useful as feedstocks in the synthesis of refrigerants and other commercial products. More particularly, such processes would provide an improvement over the current state of the art if they were capable of minimizing, or even eliminating, the production of the less desirable tetrachloropropanes and pentachloropropanes, and/or economically utilizing any amounts of the less desirable isomers that may be produced. Further benefit would be realized if the processes would provide by-products of higher commercial or reuse value than sodium chloride.

BRIEF DESCRIPTION

The present invention provides efficient processes for the production of chlorinated propenes. The processes make use of 1,2,3-trichloropropane as a feedstock and reuse at least a portion of at least one less desirable tetra- or penta-chloropropane isomer. In so doing, the processes further minimize, or even eliminate the production of the less desirable hexachloropropane isomer, 1,1,2,2,3,3-hexachloropropane. As a result, yield and/or selectivity of the process is enhanced over conventional chlorination processes that discard these isomers, and time and cost savings are thus provided. Furthermore, the processes may make use of at least one catalytic dehydrochlorination step, in place of one or more caustic dehydrochlorination step(s), and so waste water production is minimized, as is the production of the low-value by-product sodium chloride.

In one aspect, there is provided a process for the production of chlorinated propenes from a feed stream comprising 1,2,3-trichloropropane. The process comprises at least one chlorination step and at least one dehydrochlorination step. Advantageously, at least a portion of the 1,2,2,3-tetrachloropropane produced by the process is either recycled and/or further reacted, i.e., not discarded. The 1,2,2,3-tetrachloropropane may either be recycled back to the feed stream, so that the feed stream comprises 1,2,3-trichloropropane and 1,2,2,3-tetrachloropropane, or, in some embodiments, may be chlorinated in a second chlorination step to provide 1,1,2,2,3-pentachloropropane.

In some embodiments, at least one dehydrochlorination step may be conducted in the presence of a catalyst, and in such embodiments, further improvements in process productivity are expected. These embodiments also provide for the minimization of the production of the low value by-product sodium chloride, and instead, produce anhydrous HCl, which may be recovered from the process if desired. Useful chlorinating agents may include chlorine, sulfuryl chloride, or combinations of these.

The advantages provided by the present processes may be carried forward by utilizing the chlorinated and/or fluorinated propenes or higher alkenes to produce further downstream products, such as, e.g., 2,3,3,3-tetrafluoroprop-1-ene or 1,3,3,3-tetrafluoroprop-1-ene.

DESCRIPTION OF THE FIGURES

The detailed description that follows may be further understood and/or illustrated when considered along with the attached figures.

DETAILED DESCRIPTION

Figure 1:
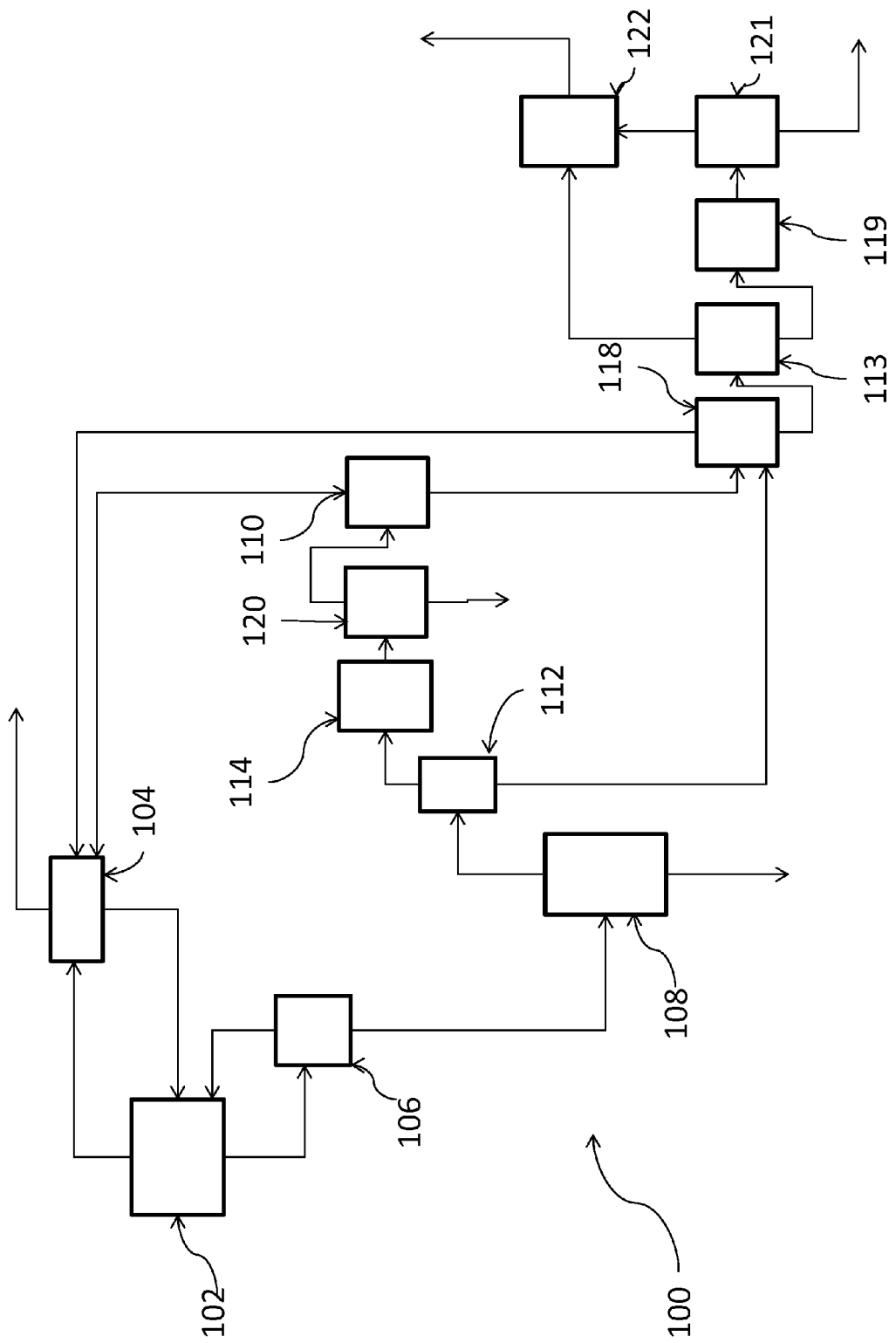
FIG. 1 is a schematic diagram of a process according to one embodiment.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

In some instances, "TCP" may be used herein as an abbreviation for 1,2,3-trichloropropane, "ACL" may be used as an abbreviation for allyl chloride or 3-chloropropene, and "TCPE" may be used as an abbreviation for 1,1,2,3-tetrachloropropene. The terms "cracking" and "dehydrochlorination" are used interchangeably to refer to the same type of reaction, i.e., one resulting in the creation of a double bond typically via the removal of hydrogen and a chlorine atom from adjacent carbon atoms in chlorinated hydrocarbon reagents.

The present invention provides efficient processes for the production of chlorinated propenes. The present processes comprise conducting at least one chlorination step and at least one dehydrochlorination step on a feedstream comprising TCP, either alone, or in some embodiments, in combination with one or more other chlorinated alkanes or alkenes, e.g., allyl chloride. At least a portion of the 1,2,2,3-tetrachloropropane generated by the process is reused within the process, i.e., is either recycled to the feedstream, or further reacted. Conventional processes have typically called for the removal of 1,2,2,3-tetrachloropropane from such processes as generated, presumably operating under the assumption that the presence of this isomer would result in the production of further undesirable by-products and/or isomers. The present inventors have now recognized that this is not the case, and that instead, use can be made of the generated 1,2,2,3-tetrachloropropane, thereby increasing the yield and efficiency of the process. Thus, the present process is more economically attractive than conventional processes that require that this isomer be removed.

Catalysts are not required for the chlorination steps of the present process, but can be used, if desired, in order to increase the reaction kinetics. For example, free radical catalysts or initiators may be used to enhance the present process. Such catalysts may typically comprise one or more chlorine, peroxide or azo-(R—N=N—R') groups and/or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, the chlorinated and/or fluorinated propene(s), within the design limitations of the reactor.

Furthermore, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Surprisingly, the utilization of the same, does not result in an increase in the production of impurities by the process, but does provide selectivities to the chlorinated propenes of at least 50%, or up to 60%, up to 70%, and in some embodiments, up to 80% or even higher.

Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15 (3-4), 333-48 and Sheppard, C. S.; Mageli, O. L. "Peroxides and peroxy compounds, organic," Kirk-Othmer Encycl. Chem. Technol., 3rd Ed. (1982), 17, 27-90.

Taking the above into consideration, examples of suitable catalysts/initiators comprising chlorine include, but are not limited to carbon tetrachloride, hexachloroacetone, chloroform, hexachloroethane, phosgene, thionyl chloride, sulfuryl chloride, trichloromethylbenzene, perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like. Diperoxides offer an advantage of not being able to propagate competitive processes (e.g., the free radical chlorination of PDC to TCP (and its isomers) and tetrachloropropanes). In addition, compounds comprising azo-groups, such as azobisisobutyronitrile (AIBN), 1,1'-azobis(cyclohexanecarbonitrile (ABCN), 2,2'-azobis(2,4-dimethyl valeronitrile), and dimethyl 2,2'-azobis(2-methylpropionate), may have utility in effecting the chlorination of PDC to trichloropropanes and tetrachloropropanes under the conditions of this invention. Combinations of any of these may also be utilized.

The process or reactor zone may be subjected to pulse laser or continuous UV/visible light sources at a wavelength suitable for inducing photolysis of the free radical catalyst/initiator, as taught by Breslow, R. in *Organic Reaction Mechanisms* W. A. Benjamin Pub, New York p 223-224. Wavelengths from 300 to 700 nm of the light source are sufficient to dissociate commercially available radical initiators. Such light sources include, e.g., Hanovia UV discharge lamps, sunlamps or even pulsed laser beams of appropriate wavelength or energy which are configured to irradiate the reactor chamber. Alternatively, chloropropyl radicals may be generated from microwave discharge into a bromochloromethane feedsource introduced to the reactor as taught by Bailleux et al., in Journal of Molecular Spectroscopy, 2005, vol. 229, pp. 140-144.

In some embodiments, ionic chlorination catalysts may be utilized in one or more chlorination steps. The use of ionic chlorination catalysts in the present process is particularly advantageous since they dehydrochlorinate and chlorinate alkanes at the same time. That is, ionic chlorination catalysts remove a chlorine and hydrogen from adjacent carbon atoms, the adjacent carbon atoms form a double bond, and HCl is released. A chlorine molecule is then added back, replacing the double bond, to provide a higher chlorinated alkane.

Ionic chlorination catalysts are well known to those of ordinary art and any of these may be used in the present process. Exemplary ionic chlorination catalysts include, but are not limited to, aluminum chloride, ferric chloride ($FeCl_3$) and other iron containing compounds, iodine, sulfur, antimony pentachloride ($SbCl_5$), boron trichloride ($BCl_3$), lanthanum halides, metal triflates, and combinations thereof. If catalysts are to be utilized in one or more of the chlorination steps of the present process, the use of ionic chlorination catalysts, such as $AlCl_3$ and $I_2$, can be preferred.

The dehydrochlorination steps of the present process may similarly be conducted without a catalyst, in the presence of a liquid caustic. Although vapor phase dehydrochlorinations advantageously result in the formation of a higher value byproduct than liquid phase dehydrochlorinations, liquid phase dehydrochlorination reactions can provide cost savings since evaporation of reactants is not required. The lower reaction temperatures used in liquid phase reactions may also result in lower fouling rates than the higher temperatures used in connection with gas phase reactions, and so reactor lifetimes may also be optimized when at least one liquid phase dehydrochlorination is utilized.

Many chemical bases are known in the art to be useful for liquid caustic cracking, and any of these can be used. For example, suitable cracking bases include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts (e.g. benzyltrimethylammonium chloride or hexadecyltributylphosphonium bromide) can also be added to improve the dehydrochlorination reaction rate with these chemical bases.

In some alternative embodiments, one or more of the dehydrochlorination steps of the present process may be carried out in the presence of a catalyst so that the use of liquid caustic is reduced, or even eliminated, from the process. In such embodiments, suitable dehydrochlorination catalysts include, but are not limited to, ferric chloride ($FeCl_3$). Other suitable examples of vapor phase dehydrochlorination catalysts known to those of ordinary skill in the art are disclosed in International Patent Application No. WO 2009/015304 A1.

Any or all of the chlorination and/or dehydrochlorination catalysts can be provided either in bulk or in connection with a substrate, such as activated carbon, graphite, silica, alumina, zeolites, fluorinated graphite and fluorinated alumina. Whatever the desired catalyst (if any), or format thereof, those of ordinary skill in the art are well aware of methods of determining the appropriate concentration and method of introduction thereof. For example, many catalysts are typically introduced into the reactor zone as a separate feed, or in solution with other reactants, e.g., TCP.

The amount of any chlorination catalyst and/or dehydrochlorination catalyst utilized will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only then, it is expected, that useful concentrations of an ionic chlorination catalyst or free radical initiator will range from 0.001% to 20% by weight, or from 0.01% to 10%, or from 0.1% to 5 wt. %, inclusive of all subranges therebetween. If a dehydrochlorination catalyst is utilized for one or more dehydrochlorination steps, useful concentrations may range from 0.01 wt. % to 5 wt. %, or from 0.05 wt. % to 2 wt. % at temperatures of from 70° C. to 200° C. If a chemical base is utilized for one or more dehydrochlorinations, useful concentrations of these will range from 0.01 to 20 grmole/L, or from 0.1 grmole/L to 15 grmole/L, or from 1 grmole/L to 10 grmole/L, inclusive of all subranges therebetween. Concentrations of each catalyst/base are given relative to the feed, e.g., 1,2,3-trichloropropane.

The present process can make use of a feedstock comprising 1,2,3-trichloropropane to produce the desired chlorinated propenes. The process feedstock may also comprise recycled alkanes, including recycled 1,2,2,3-tetrachloropropane, or other chlorinated alkanes, if desired. And, the 1,2,3-trichloropropane may be generated within, or upstream of, the process, if desired, by any methods known to those of ordinary skill in the art.

The chlorination steps of the process may be carried out using any chlorination agent, and several of these are known in the art. For example, suitable chlorination agents include, but are not limited to chlorine, and/or sulfuryl chloride ($SO_2Cl_2$). Combinations of chlorinating agents may also be used. Either or both $Cl_2$ and sulfuryl chloride may be particularly effective when aided by the use of the aforementioned ionic chlorination catalysts.

Any chlorinated propene may be produced using the present method, although those with 3-5 chlorine atoms are particularly commercially attractive, and production of the same may thus be preferred in some embodiments. In some embodiments, the process may be used in the production of 1,1,2,3-tetrachloropropene, which may be a preferred feedstock for refrigerants, polymers, biocides, etc.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, etc.

That being said, the particular conditions employed at each step described herein are not critical, and are readily determined by those of ordinary skill in the art. What is important is that at least a portion of any 1,2,2,3-tetrachloropropane generated by the process is utilized by the process, i.e., either recycled as is, further reacted, or further reacted and recycled. It is also advantageous that at least one dehydrochlorination step be conducted catalytically, rather than by using liquid caustic, so that anhydrous HCl is produced and the production of sodium chloride is minimized. Those of ordinary skill in the art will readily be able to determine suitable equipment for each step, as well as the particular conditions at which the chlorination, dehydrochlorination, separation, drying and isomerization steps may be conducted.

In the present process, 1,2,3-trichloropropane is converted to TCPE using at least one chlorination step and at least one dehydrochlorination step. Importantly and advantageously, at least a portion of any 1,2,2,3-tetrachloropropane generated by the process is utilized within the process. That is, at least a portion of any 1,2,2,3-tetrachloropropane may be recycled to the feedstock, or further reacted to provide intermediates more useful in the production of TCPE.

More specifically, and in one exemplary embodiment, a feed stream comprising TCP is fed to a liquid phase chlorination reactor, e.g., such as a batch or continuous stirred tank reactor with an internal cooling coil. A shell and multitube reactor followed by vapor liquid disengagement tank or vessel can also be used. Suitable reaction conditions include, e.g., temperatures of from ambient temperature (e.g., 20° C.) to 200° C., or from 30° C. to 150° C., or from 40° C. to 120° C. or from 50° C. to 100° C. Ambient pressure may be used, or pressures of from 100 kPa to 1000 kPa, or from 100 kPa to 500 kPa, or from 100 kPa to 300 kPa. At such conditions, the TCP is chlorinated to tetra- and pentachlorinated propanes at per pass conversions of greater than 10%, or 30%, or 50%, or 60%, or even up to 80% can be seen. The per pass conversion and reaction conditions are chosen or optimized such that the products of the first chlorination step consist of a mixture of tetrachloropropane and pentachloropropane while minimizing the formation of hexachloropropane to less than 10%.

The chlorination(s) may be conducted neat, i.e., in the absence of solvent, or, one or more solvents may be provided to the chlorination reactor, and may be provided as a component of the feedstock, or, recycled from one or more separation columns operatively disposed to receive streams from the chlorination reactor. For example, chloropropane intermediates may be recycled back to the chlorination reactor from one separation column, and tri- and tetrachloropropane intermediates may be recycled from another separation column. In addition, or as an alternative, the chlorination reactor may be provided with a feed of any solvent appropriate for chlorination reactions, such as, e.g., carbon tetrachloride, sulfuryl chloride, 1,1,2,3,3-pentachloropropane, 1,1,2,2,3,3-hexachloropropane, other hexachloropropane isomers, or a combination of these. In some embodiments, at least a portion of the 1,2,2,3-tetrachloropropane that is generated by, and reused within, the process is recycled to the first chlorination reactor.

The overhead vapor from the chlorination reactor, is cooled, condensed and fed to a first separation column, e.g., a distillation column that may be used to recover anhydrous HCl from an overhead stream thereof. This separation column is operated at conditions effective to provide anhydrous HCl to an overhead line thereof and chlorine through a bottom recycle line.

More particularly, the top temperature of separation column for the recovery of HCl may typically be set below 0° C. or more preferably, can be set at a temperature of from −70° C. to −10° C. The bottom temperature of such a column is desirably set at from 10° C. to 150° C., or from 30° C. to 100° C., with the exact temperature dependent to some degree on the bottom mixture composition. The pressure of this separation column is desirably set above 200 kPa or preferably, from 500 kPA to 2000 kPa, or more preferably from 500 kPa to 1000 kPa. The bottom stream of a column operated at such conditions would be expected to contain excess chlorine, unreacted TCP, while the overhead stream would be expected to comprise anhydrous HCl.

The bottoms liquid product stream from the first chlorination reactor may be fed to a second separation column operated at conditions effective to separate the unreacted TCP and tetrachloropropane isomers from the 1,1,2,3-tetrachloropropane, pentachloropropanes, and heavier byproducts. Such a separation may be achieved, e.g., by feeding the bottoms liquid stream to a separation column operating with a reboiler temperature lower than 180° C. and at a pressure at or less than atmospheric.

The tetrachloropropane isomers are then desirably separated into at least two streams—one stream comprising 1,2,2,3-tetrachloropropane (having a boiling point of 163° C.) and unreacted TCP (having a boiling point of 157° C.) and the other comprising 1,1,2,3-tetrachloropropane (having a boiling point of 179° C.). The 1,1,2,3-tetrachloropropane may then be dehydrochlorinated as described in the art, e.g., by U.S. Pat. No. 3,823,195.

Advantageously, the stream of TCP and 1,2,2,3-tetrachloropropane may then be recycled to the first chlorination reactor, or, separated to provide streams comprising TCP and 1,2,2,3-tetrachloropropane, e.g., via a separation column operating with a bottoms temperature of lower than 165° C. and at a pressure at or less than atmospheric. In the latter embodiment, the separated TCP is then recycled to the first chlorination reactor and the 1,2,2,3-tetrachloropropane further chlorinated to provide 1,1,2,2,3-pentachloropropane, or dehydrochlorinated and chlorinated to provide 1,1,2,2,3-pentachloropropane. Either embodiment is advantageous over conventional methods that call for the removal and disposal of this isomer.

If the thus separated 1,2,2,3-tetrachloropropane is desirably further chlorinated, rather than, or in addition to, a portion it being recycled, such a chlorination may desirably be carried out in a liquid phase chlorination reactor separate from, and operated at different conditions than, the first chlorination reactor. More specifically, 1,2,2,3-tetrachloropropane may be chlorinated to provide 1,1,2,2,3-pentachloropropane by feeding the same to a continuous stirred tank reactor operated at conditions sufficient to provide from 10% to 80%, or preferably from 10% to 40% per pass conversion of 1,2,2,3-tetrachloropropane at the reactor effluent, e.g., at a temperature of from 30° C. to 120° C. and at pressures of ambient pressure or higher. When so operated, this chlorination reaction would be expect to provide conversions of 1,2,2,3-tetrachloropropane of less than 80% with selectivity to 1,1,2,2,3-pentachloropane of from 0% to 95%.

The output from the second chlorination reactor may then be fed to a separation column operated at conditions effective to separate the second chlorination reaction stream into an overhead stream comprising chlorine and HCl and a bottoms stream comprising unreacted 1,2,2,3-tetrachloropropane, the desired pentachloropropane isomers and heavier by-products. The overhead stream may be further separated and purified to provide a stream of chlorine, which may be recycled to the first chlorination reactor, if desired, and a stream of HCl, which may be provided to the first separation column for the recovery of anhydrous HCl, as described above.

The bottoms stream from the second chlorination reactor may be fed to the second separation column that also receives feed from the first chlorination reactor. The bottom stream of this column comprises products with boiling points higher than 1,2,2,3-tetrachloropropane, e.g. 1,1,2,3-tetrachloropropane, pentachloropropanes, and heavier byproducts. This bottom stream is then fed to a third separation column operated such that the overhead stream comprises 1,1,2,3-tetrachloropropane and the bottom stream comprises pentachloropropanes isomers and heavier byproducts. As well known in the art, this overhead stream can then be dehydrochlorinated using caustic to produce trichloropropene isomers, e.g., as described in U.S. Pat. No. 3,823,195.

The trichloropropenes from the bottoms stream can then be further chlorinated to pentachloropropane isomers in a separate chlorination reactor operated at a temperature of from 50° C. to 80° C. The resulting pentachloropropanes are then combined with the bottom stream of a third separation column comprising other pentachloropropane intermediates.

As an alternative to chlorinating the 1,2,2,3-tetrachloropropane to 1,1,2,2,3-pentachloropropane, this tetrachloropropane isomer can be dehydrochlorinated at high yield to 1,2,3-trichloropropene. This trichloropropane intermediate is then readily chlorinated in liquid phase to 1,1,2,2,3-pentachloropropane as known in the art. In this case, the 1,2,2,3-tetrachloropropane can be optionally be combined with 1,1,2,3-tetrachloropropane before the caustic dehydrochlorination step describe above.

The bottom stream of the third separation column comprising pentachloropropanes isomers is then further fed to a fourth separation column operated at conditions effective to provide a bottom stream comprising the less desirable pentachloropropane isomer, 1,1,2,3,3-pentachloropropane, and heavier chlorinated reaction products, which is purged, and an overhead stream comprising the desirable pentachloropropane isomers, 1,1,1,2,3-pentachloropropane and 1,1,2,2,3-pentachloropropane. In some embodiments, this overhead stream can then be catalytically dehydrochlorinated, e.g., using iron or an iron containing catalyst, such as $FeCl_3$ so that the high value by-product anhydrous HCl is produced. In other embodiments, the overhead stream can be dehydrochlorinated to the desired tetrachloropropane product(s) using caustic or other chemical bases, as described above.

More specifically, a catalytic dehydrochlorination reactor may typically be a batch or a continuous stirred tank reactor. The mixing can be done, e.g., by mechanical or jet mixing of feed streams. Those of ordinary skill in the art are readily able to determine the appropriate conditions at which to run a dehydrochlorination reactor in order to conduct the aforementioned dehydrochlorination. The catalytic dehydrochlorination of 1,1,1,2,3-pentachloropropane provides 2,3,3,3-tetrachloropropene and 1,1,2,3-tetrachloropropene, as well as HCl that may advantageously be recovered by recycling the waste stream from the reactor to the initial anhydrous HCl recovery column.

The reaction stream from the catalytic dehydrochlorination reactor is then fed to a further separation column to separate the desired chlorinated propene, e.g., 1,1,2,3-TCPE, from the remaining stream, which is expected to comprise mostly 1,1,2,2,3-pentachloropropane. This stream of 1,1,2,2,3-pentachloropropane is then caustic cracked to provide a mixture of 1,1,2,3-TCPE and 2,3,3,3-TCPE. The reaction stream from the caustic dehydrochlorination reactor may optionally be fed to a drying column, and the dried stream therefrom provided to a further reactor to isomerize the 2,3,3,3-tetrachloropropene to 1,1,2,3-tetrachloropropene under the appropriate conditions.

For example, catalysts may be utilized to assist in the isomerization, in which case, suitable catalysts include, but are not limited to (i) siliceous granules having a polar surface including kaolinite, bentonite, and attapulgite; (ii) other mineral salts of silica such as saponite, quartz, (iii) siliceous non-mineral substance such as silica gel, fumed silica, and glass, or combinations of any of these. Suitable conditions for drying columns for such reaction streams are also known to those of ordinary skill in the art, as evidenced by U.S. Pat. No. 3,926,758

A schematic illustration of such a process is shown in FIG. 1. As shown in FIG. 1, process 100 would make use of chlorination reactors 102 and 110, separation columns 104, 106, 108, 112, and 113, dehydrochlorination reactors 114, 118 and 119, dryers 120 and 121 and isomerization reactor 122. In operation, 1,2,3-trichloropropane (alone or, in some embodiments, in combination with recycled 1,2,2,3-tetrachloropropane and/or allyl chloride) and the desired chlorination agent (e.g., chlorine, $SO_2Cl_2$, or combinations of these) are fed to chlorination reactor 102, which may be operated at any set of conditions operable to provide for the chlorination of allyl chloride to TCP and/or the chlorination of TCP to tetra- and pentachlorinated propanes and known to those of ordinary skill in the art.

The overhead stream of chlorination reactor 102 is provided to separation column 104, which may desirably be a distillation column. The feed to the HCl separation column is preferably totally condensed liquid at temperature −40° C. to 0° C. made by applying a fractionation method such as that described in U.S. Pat. No. 4,010,017. Separation column 104 is operated at conditions effective to provide anhydrous HCl through an overhead line thereof and chlorine and unreacted TCP to chlorination reactor 102.

The bottom stream of reactor 102 is provided to separation column 106, which is operated at conditions effective to provide an overhead stream comprising TCP and 1,2,2,3-tetrachloropropane and a bottoms stream comprising other tetrachloropropane isomers, pentachloropropanes and heavier reaction by-products. The overhead stream from separation column 106 may be recycled to first chlorination reactor 102, while the bottoms stream from separation column 106 is fed to further separation column 108.

Separation column 108 separates the bottom stream from separation column 106 into an overhead stream comprising 1,1,2,3-tetrachloropropane and the desirable pentachloropropane isomers (1,1,2,2,3-pentachloropropane and 1,1,1,2,3-pentachloropropane) and a bottom stream comprising the less desirable 1,1,2,3,3-pentachloropropane, hexachloropropane and heavier by-products. The overhead stream is fed to separation column 112, while the bottoms stream is appropriately disposed of.

Separation column 112 separates the overhead stream from separation column 108 into an overhead stream comprising 1,1,2,3-tetrachloropropane and a bottoms stream comprising desired pentachloropropanes isomers, e.g., 1,1,2,2,3 and 1,1,1,2,3-pentachloropropane. The 1,1,2,3-tetrachloropropane is then caustic cracked in dehydrochlorination reactor 114 to provide trichloropropene intermediates.

The reaction liquid from dehydrochlorination reactor 114 is fed to dryer column 120 and the dried stream fed to chlorination reactor 110. Excess chlorine from chlorination reactor 110 may be recycled to separation column 104, if desired. The product stream from chlorination reactor 110, expected to comprise 1,1,2,2,3 and 1,1,1,2,3-pentachloropropane, is fed to dehydrochlorination reactor 118, where it is combined with the bottoms from stream separation column 112 that also comprises 1,1,2,2,3- and 1,1,1,2,3-pentachloropropane.

Within dehydrochlorination reactor 118, the desirable pentachloropropane isomers are catalytically dehydrochlorinated to provide 2,3,3,3-tetrachloropropene and 1,1,2,3-tetrachloropropene. More specifically, dehydrochlorination reactor may be charged with, e.g., iron or an iron containing catalyst such as $FeCl_3$ and operated at pressures of from ambient to 400 kPA, at temperatures of from 40° C. to 150° C. and with residence times of less than 3 hours.

The bottom reaction stream from dehydrochlorination reactor 118 is fed to separation column 113, while the overhead stream, comprising anhydrous HCl, is provided to separation column 104 for purification and recovery of anhydrous HCl. The bottom stream from dehydrochlorination reactor 118, comprising tetrachloropropene products and unreacted pentachloropropanes, is then fed to separation column 113.

Separation column 113 is operated at conditions effective to separate the desired chlorinated propene, e.g., 1,1,2,3-TCPE, as an overhead stream from the remaining by-products, e.g., 1,1,2,2,3-pentachloropropane. The bottoms stream from separation column 113 is fed to caustic dehydrochlorination reactor 119, and the product stream thereof provided to drying column 121. The dried stream from drying column 121 is provided to isomerization reactor 122 to isomerize the 2,3,3,3-tetrachloropropene to 1,1,2,3-tetrachloropropene under the appropriate conditions.

Figure 2:
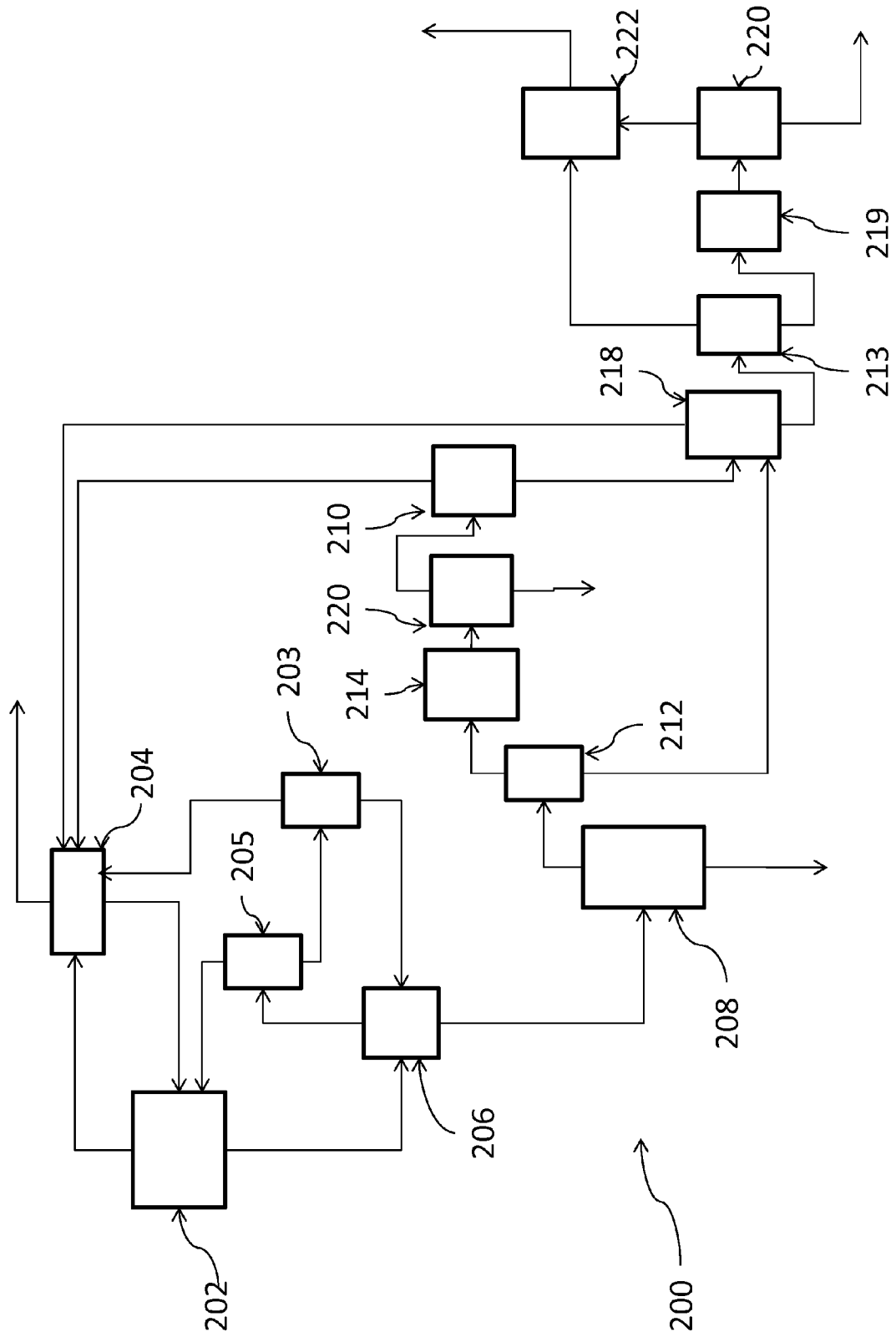
FIG. 2 is a schematic diagram of a process according to a further embodiment.

An additional embodiment of the process is shown in FIG. 2. This process is very similar to that shown in FIG. 1, with the exception of the inclusion of additional separation column 205 and third chlorination reactor 203. In operation, rather than recycling the overhead stream from separation column 206 to chlorination reactor 202, the overhead stream from separation column 206 is fed to separation column 205. Separation column 205 is operated such that the overhead stream, expected to comprise unreacted TCP and 1,2,2,3-tetrachloropropane, is separated to an overhead stream comprising TCP, recycled back to first chlorination reactor 202, and a bottoms stream comprising 1,2,2,3-tetrachloropropane. The bottoms stream is fed to third, liquid phase chlorination reactor 203, wherein it is used to produce an overhead stream comprising HCl and a bottoms stream comprising unreacted 1,2,2,3-tetrachloropropane and 1,1,2,2,3-pentachloropropane. The overhead stream from chlorination reactor 203 is fed to separation column 204 that provides anhydrous HCl through an overhead line, while the bottoms stream is fed back to separation column 206 to recover the unreacted tetrachloropropane reactant.

In this example, third chlorination reactor 203 is desirably operated at different conditions than the first chlorination reactor 202, i.e., chlorination reactor 203 is desirably operated at conditions such that the production of hexachloropropane is minimized in the bottom stream. As a result, the overall yield of the process is improved.

The chlorinated propenes produced by the present process may typically be processed to provide further downstream products including hydrofluoroolefins, such as, for example, 1,3,3,3-tetrafluoroprop-1-ene (HFO-1234ze). Since the present invention provides an improved process for the production of chlorinated propenes, it is contemplated that the improvements provided will carry forward to provide improvements to these downstream processes and/or products. Improved methods for the production of hydrofluoroolefins, e.g., such as 2,3,3,3-tetrafluoroprop-1-ene (HFO-1234yf), are thus also provided herein.

The conversion of chlorinated propenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of a chlorinated propene is fluorinated in a catalyzed, gas phase reaction to form a compound such as 1-chloro-3,3,3-trifluoropropene (1233zd). The 1-chloro-2,3,3,3-tetrafluoropropane is then dehydrochlorinated to 2,3,3,3-tetrafluoroprop-1-ene or 1,3,3,3-tetrafluoroprop-1-ene via a catalyzed, gas phase reaction.

Example 1.

50 mL 123-trichloropropane and 500 mg dimethyl 2,2'-azobis(2-methylpropionate) are added to a tubular reactor at a pressure of 150 psig. The reactor is sealed and $Cl_2$ flow started (30% v/v, 200 sccm). The reactor is then heated to 70° C. After 200 min at 70° C., 23% conversion of the TCP is observed, with the product stream comprising 1,1,2,3-tetrachloropropane, 1,2,2,3-tetrachloropropane, 1,1,2,2,3-pentachloropropane, and 1,1,2,3,3-pentachloropropane (11233), with selectivities of 59.7%, 37.2%, 2.0%, and 1.2% respectively. The 1,1,2,3-tetrachloropropane is then separated from the product mixture and the reactor purged.

Carbon tetrachloride (45 mL) is added to the reactor and the reactor sealed and pressurized to 150 psi using $Cl_2$ (30% in $N_2$). Additional $Cl_2$ is added for ~20 minutes and then the reactor is heated to 70° C. The reactor was sealed (reactor pressure ~150 psig) and a mixture of the 1,2,2,3-tetrachloropropane (1223) (3 mL) provided as described above, $CCl_4$ (7 mL) and dimethyl 2,2'-azobis(2-methylpropionate) (20 mg) is added (t=0). The mixture is stirred at 70° C. for ~90 minutes and samples are periodically taken. Table 1, below, shows the product distribution, expressed as molar % of the total product stream, as a function of time. As shown by Table 1, recycling of the 1,2,2,3-tetrachloropropane produced in a first chlorination reaction, to a further chlorination reaction wherein the 1,2,2,3 conversion is less than, e.g., 20%, results in the production of the desired intermediate 1,1,2,2,3-pentachloropropane (11223) with less than 3.3% molar selectivity to the undesired 1,1,2,2,3,3-hexachloropropane (112233).

TABLE 1

| Time (min) | 5 | 21 | 60 |
|---|---|---|---|
| 1,2,2,3-tetrachloropropane | 94.28 | 89.77 | 82.68 |
| 1,1,2,2,3-pentachloropropane | 5.64 | 10.01 | 16.75 |
| 1,1,2,2,3,3-hexachloropropane | 0.08 | 0.22 | 0.57 |
| Selectivity to 1,1,2,2,3-pentachloropropane (%) | 98.6 | 97.9 | 96.7 |

The invention claimed is:

1. A process for the production of chlorinated propenes from a feedstream comprising 1,2,3-trichloropropane, comprising at least one chlorination step and at least one dehydrochlorination step, wherein 1,2,2,3-tetrachloropropane produced by the process is recycled and/or further reacted.

2. The process of claim 1, wherein the chlorination step produces a mixture comprising tetrachloropropanes and pentachloropropanes.

3. The process of claim 2, wherein the mixture is separated to provide a stream comprising the 1,2,2,3-tetrachloropropane.

4. The process of claim 3, wherein the 1,2,2,3-tetrachloropropane stream is recycled to the first chlorination step.

5. The process of claim 3, wherein the 1,2,2,3-tetrachloropropane stream is chlorinated in a second chlorination step to provide 1,1,2,2,3-pentachloropropane.

6. The process of claim 3, wherein the separation further provides a stream of unreacted 1,2,3-trichloropropane that is recycled to a chlorination step.

7. The process of claim 3, wherein the separation further provides a stream of HCl and a stream comprising unreacted $Cl_2$, wherein the HCl is recovered from the process as anhydrous HCl and the $Cl_2$ is recycled.

8. The process of claim 3, wherein the separation further provides a stream comprising 1,1,2,3-tetrachloropropane and a stream comprising pentachloropropane isomers and heavier byproducts.

9. The process of claim 8, wherein the stream comprising 1,1,2,3-tetrachloropropane is dehydrochlorinated to produce a stream comprising trichloropropene, and the trichloropropene stream is chlorinated to produce a stream comprising 1,1,1,2,3-pentachloropropane and 1,1,2,2,3-pentachloropropane.

10. The process of claim 1, wherein the at least one chlorination step is carried out in the presence of a free radical initiator comprising, azobisisobutyronitrile, 1,1'-azobis(cyclohexanecarbonitrile), 2,2'-azobis(2,4-dimethyl valeronitrile), and dimethyl 2,2'-azobis(2-methylpropionate), or a combination of these.

11. The process of claim 1, wherein the at least one dehydrochlorination is carried out in the presence of dehydrochlorinating catalyst comprising iron, ferric chloride, aluminum chloride, or a combination of these.

12. The process of claim 3, wherein the remainder of the mixture is dehydrochlorinated to provide a stream comprising 1,1,2,3-tetrachloropropene, 2,3,3,-tetrachloropropane, HCl and unreacted pentachloropropanes.

13. The process of claim 12, wherein the unreacted pentachloropropanes are dehydrochlorinated to provide a mixture comprising 1,1,2,3-tetrachloropropene.

14. The process of claim 3, wherein the 1,2,2,3-tetrachloropropane is recycled to a dehydrochlorination step to produce 1,2,3-trichloropropene, and the 1,2,3-trichloropropene is chlorinated to produce 1,1,2,2,3-pentachloropropane.

* * * * *